(12) United States Patent
Vranić

(10) Patent No.: US 10,716,483 B2
(45) Date of Patent: Jul. 21, 2020

(54) METHOD AND SYSTEM FOR VECTOR ANALYSIS OF ELECTROCARDIOGRAMS

(71) Applicant: Ivana I. Vranić, Belgrade (RS)

(72) Inventor: Ivana I. Vranić, Belgrade (RS)

(73) Assignee: Ivana I. Vranic, Belgrade (RS)

( * ) Notice: Subject to any disclaimer, the term of this patent is extended or adjusted under 35 U.S.C. 154(b) by 40 days.

(21) Appl. No.: 15/267,921

(22) Filed: Sep. 16, 2016

(65) Prior Publication Data

US 2017/0049346 A1 Feb. 23, 2017

Related U.S. Application Data

(63) Continuation-in-part of application No. 14/766,707, filed as application No. PCT/RS2013/000005 on Apr. 5, 2013, now abandoned.

(30) Foreign Application Priority Data

Feb. 8, 2013 (RS) .................................. P-2013/0048
Mar. 12, 2013 (RS) .................................. P-2013/0082

(51) Int. Cl.
*A61B 5/04* (2006.01)
*A61B 5/0456* (2006.01)
(Continued)

(52) U.S. Cl.
CPC ...... *A61B 5/04012* (2013.01); *A61B 5/04011* (2013.01); *A61B 5/0456* (2013.01); *A61B 5/0472* (2013.01); *A61B 5/0006* (2013.01)

(58) Field of Classification Search
CPC . A61B 5/04012; A61B 5/0472; A61B 5/0411; A61B 5/0456
See application file for complete search history.

(56) References Cited

U.S. PATENT DOCUMENTS

| 7,266,408 | B2 * | 9/2007 | Bojovic | ............. | A61B 5/04011 600/512 |
| 7,424,137 | B2 * | 9/2008 | Badilini | ............... | A61B 5/0402 382/128 |

(Continued)

FOREIGN PATENT DOCUMENTS

| WO | 2012106729 A1 | 8/2012 |
| WO | 2014123438 A1 | 8/2014 |

OTHER PUBLICATIONS

Peters S et al: "Prognostic value of QRS fragmentation in patients with arrhythmogenic right ventricular cardiomyopathy/dysplasia", Journal of Cardiovascular Medicine, USA, vol. 13, No. 5, May 1, 2012. pp. 295-298.

Edenbrandt L et al: "Vectorcardiographic bites—A method for detection and quantification applied on a normal material", Journal of Electrocardiology, Elsevier Science, XX, vol. 22, No. 4, Oct. 1, 1989. pp. 325-331.

(Continued)

*Primary Examiner* — William J Levicky
(74) *Attorney, Agent, or Firm* — The Watson IP Group, PLC; Jovan N. Jovanovic

(57) ABSTRACT

A method for vector analysis of an electrocardiogram for assessment of risk of sudden cardiac death includes receiving data about electrical activity of heart of a subject recorded on electrocardiogram device, generating a vector cardiogram based on the data, analyzing the vector cardiogram to determine arrhythmogenic right ventricular dysplasia/cardiomyopathy to identify a presence of a micro-scar in a three-dimensional vector loop of the vector cardiogram, determining a risk of SCD for the subject based on the identification of the presence of a micro-scar, and storing the risk in a database.

9 Claims, 10 Drawing Sheets

(51) Int. Cl.
 *A61B 5/0472* (2006.01)
 *A61B 5/00* (2006.01)

(56) References Cited

U.S. PATENT DOCUMENTS

| | | | |
|---|---|---|---|
| 9,265,437 B2* | 2/2016 | Wei | A61B 5/04011 |
| 2002/0115916 A1 | 8/2002 | Sjoqvist | |
| 2009/0177102 A1* | 7/2009 | Schneider | A61B 5/0452 600/516 |
| 2011/0144510 A1* | 6/2011 | Ryu | A61B 5/042 600/509 |
| 2011/0251504 A1 | 10/2011 | Tereshchenko et al. | |
| 2013/0096394 A1* | 4/2013 | Gupta | A61B 5/0452 600/518 |

OTHER PUBLICATIONS

Martini B et al: "Vectorgraphic Analysis of Late Potentials", Giornale Italiano Di Cardiologia, Pozzi, Rome, IT, vol. 16, No. 2, Jul. 1, 1986. pp. 565-572.

International Bureau, Notification of the Recording of a Change for Application No. PCT/RS2013/000005, dated Jan. 28, 2014.

European Patent Office, International Search Report for Application No. PCT/RS2013/000005, dated Nov. 6, 2013.

International Bureau, Notification Concerning Submission, Obtention or Transmittal of Priority Document for Application No. PCT/RS2013/000005, dated Aug. 22, 2013.

International Bureau, Notification Concerning the Filing of Amendments of the Claims for Application No. PCT/RS2013/000005, dated Jan. 28, 2014.

* cited by examiner

Q wave

R wave

S wave

ST segment

METHOD AND SYSTEM FOR VECTOR ANALYSIS OF ELECTROCARDIOGRAMS

RELATED APPLICATION INFORMATION

This patent is a continuation in part of application Ser. No. 14/766,707, filed Aug. 7, 2015, titled A METHOD AND SYSTEM FOR VECTOR ANALYSIS OF ELECTROCARDIOGRAM IN ASSESSMENT OF RISK OF SUDDEN CARDIAC DEATH (SCD) DUE TO ARRHYTHMOGENIC RIGHT VENTRICULAR DYSPLASIA/CARDIOMYOPATHY BY QUANTIFYING MICRO SCARS (I.E. "BITES") IN THREE DIMENSIONAL VECTOR LOOPS, which claims priority from Patent Cooperation Treaty Application No. PCT/RS2013/000005, filed Apr. 5, 2013, titled A METHOD AND SYSTEM FOR VECTOR ANALYSIS OF ELECTROCARDIOGRAM IN ASSESSMENT OF RISK OF SUDDEN CARDIAC DEATH (SCD) DUE TO ARRHYTHMOGENIC RIGHT VENTRICULAR DYSPLASIA/CARDIOMYOPATHY BY QUANTIFYING MICRO SCARS (I.E. "BITES") IN THREE DIMENSIONAL VECTOR LOOPS, which claims the benefit of priority to Serbian Patent Application No.: P-2013/0048 filed Feb. 8, 2013 and Serbian Patent Application No.: P-2013/0082 filed Mar. 12, 2013. The full contents of the International Application are incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD

This disclosure relates to diagnostic measurement of heart and/or pulse rhythm.

BACKGROUND

In the evaluation of heart signals expressed through vectors in time and space, a significant role belongs to electrode positioning 100 on arbitrarily agreed precise locations, as shown in FIG. 1. Depending on the type of electrocardiogram ("EKG") recorder, Einthoven bipolar leads D1, D2, and D3 with Baily triaxial system of amplification are in use: aVR, aVL, and aVF (which essentially do not change merits in mathematical sense), so that an EKG inscription is being read from different angle perspectives in 6 xtremity leads of 60 degrees angles, as shown in FIG. 2. An additional 6 leads, VI, V2, V3, V4, V5 and V6, are obtained from a unipolar recording system for measuring, as shown in FIG. 3.

An EKG of a healthy person includes the P wave, QRS complex (including Q, R and S waves) and T wave, as shown in FIG. 4. The real waves are the P wave and the T wave. They can be positive, negative or biphasic. A Q wave is negative, an R wave is positive, and the S wave is negative. Specific wave type is determined on the basis of the R wave location in the following manner if a negative wave precedes the positive R wave then it is the Q wave. If a negative wave follows after R wave, then it is an S wave. Otherwise, in a normal QRS complex, there is no more than one positive wave (i.e., the R wave). If other R waves exist, as it is generally in pathological states, they are denoted R. If there is only one negative wave, without the positive R wave, then it is not clear whether it is the S or the Q wave, so it is called a QS wave or complex.

Fast and large changes in the size and direction of total dipole that are generated during ventricular depolarization result in a QRS complex seen on an EKG. A normal process is shown in FIG. 5. The start of ventricular depolarization usually happens on the left side of the medial part of interventricular septum. Analysis of heart dipole which is further generated by initial depolarization, with an aid of Einthoven's triangle, shows that this dipole has negative a component on lead I, a small negative component on lead II and a positive component on lead III. On FIG. 5, one may spot how dipoles make opposite deflection in individual leads. For example, the Q wave appears in leads I and II, but not in lead III. The second row in this picture shows both ventricles during instantaneous ventricular depolarization in the moment of the largest number of total dipole with the most similar orientation. This phase creates a large total dipole, which is responsible for the R wave on an EKG. Such a dipole is almost parallel with lead II.

As it is shown, such dipole creates a big positive R wave on all three leads. The third row in FIG. 5 shows a situation at the end of a depolarizing spread through chambers and shows how a small total dipole is at that very instant in the S wave creation. The S wave is not necessarily present in all leads. The bottom line shows that during ST segment formation, all cells within both chambers are in a depolarized state. There is no wave of electrical activity that is transmitted through the heart tissue. There is no total dipole (i.e. difference between two body surface points regarding electrical potential). An EKG record is flat at that point, i.e. isoelectrical.

Arrhythmogenic right ventricular dysplasia/cardiomyopathy ("ARVD/C") is a genetic disorder which is associated with concealed involvement of the right chamber ("RV") and its structural and functional changes (which are the result of such replacement of heart tissue with fat and fibrous tissue), and electrical insta-bility causes ventricular arrhythmias and sudden cardiac death ("SCD"). Sudden cardiac death is a natural death caused by problems with the heart preceded by loss of consciousness, which lasts about an hour and is a consequence of the acute heart problems. Sudden cardiac death often occurs in people who are generally healthy. Those who die a sudden death, probably are never aware of the potential risk they carry. Frequency of sudden cardiac death with unknown cause is estimated to be between 1/2000 people to 7/1000 people and can af-fect any age, sex, geographic or socioeconomic position. SCD is somewhat less common in USA than in Europe. In Europe, SCD is somewhat more frequent in the Mediterranean region, than in the northern part of Europe, due to population migrations through history. Endemic regions are Veneto in northern Italy with 80% of incidence and island Naxos in Greece with 50% of incidence.

Noninvasive and invasive methods for evaluation of the shape and function of the RV have inherent limitations, due to the complex construction of its shape. Examination of the RV could be a difficult task for a clinical doctor, considering its geometric complexity and that it is divided into three parts: in-flow, outflow and an RV body, which is falciform and abbreviated. The free wall of the RV may have more or less trabeculations, which in combination to its ret-rosternal position limit precise chamber measuring and determination of wall thickness. Tricuspid anterio-postrior systolic excursion ("TAPSE") has been shown to correlate well with global function (in adult population) as ejectional fraction of left ventricle ("EF LV") whereas objectively assessed by radionuclide ventriculography (done by standard way). Recognizing mild, frusta, or localized forms, remains a clinical challenge. It is difficult to diagnose ARVD/C in a patient with minimal involvement of the RV on heart ultrasound or contrast angiography. So far, only "V sign" on heart ultrasound has been attributed as pathognomonic. The recommended criteria for ARVD/C early phase detection from World Health Organization (and its working group on ARVD/C) have been found insufficient for this matter. The early identification of sport players who carry genes for ARVD/C plays a central role in the prevention of SCD during sports activities. Most frequent clinical manifestations of the disease are depolarize-repolarize changes on EKG, mainly localized in right precordial leads, global regional morphologic or functional changes of the RV and arrhythmias coming from the RV. Even an asymptomatic person can be diagnosed based on a positive EKG change and ventricular arrhythmia.

An EKG record has technical restrictions in diagnostic span with respect to the analysis of an aggregate value of vector trajectories in each instant of propagation of the electrical heart dipoles. Conversely, a vectorcardiogram ("VCG") record is an attempt for objectification of relativity of differences in potential in standard EKG devices to maximize its diagnostic capacity. In other words, vector cardiogram represents a "tridimensional electrocardiogram".

The vectorcardiographic appearance of an EKG represents a stereo metric loop (i.e., a closed curve or trajectory), which is usually shown in separate planes defined by an appropriate axis (frontal: X,Y), (sagittal: Y,Z) and (horizontal: X,Z), as shown in FIG. 6. However, not all signal value is seen from the aspect of separate two-dimensional planes, but it is necessary to observe the loop in three-dimensions. This offers the maximum usability of an analyzed signal in diagnostic and therapeutic sense, because vectorcardiography overcomes imperfections of a typical EKG approach and provides a view of a larger real picture, as shown in FIG. 7.

The reason for this is that every moment some part of atrial or ventricular heart muscle produces a small amount of the electrical force, directed up or down, right or left; and since the heart is a tridimensional structure, the electrical force also moves forwards or backwards. Spatially oriented electrical forces which are generated by the heart appear in a certain order, but not simultaneously.

The form and magnitude of the P wave, QRS complex, ST segment and T wave are set by management direction of aggregate vector and separate vector resultants determined by the location of unipolar precordial leads. A central direction of a depolarization process reflects the sum of all vectors in each part of ventricular myocardium.

DETAILED DESCRIPTION

Methods described herein enable diagnosis of risk of sudden cardiac death syndrome ("SCD") due to arrhythmogenic right ventricular dysplasia/cardiomyopathy in a timely manner. Vector analysis of electrocardiograms is used for assessment of risk of SCD due to arrhythmogenic right ventricular dys-plasia/cardiomyopathy by quantifying micro scars (i.e. "bites"), where each micro scar represents deviation from an ideal curve as observed in a three-dimensional vector loop. Micro scars were first perceived in patients with diabetes mellitus, in whom small areas of fibrosis or necrosis in the heart were found at autopsy, which was the basis for the hypothesis that micro scars represent the expression of small myocardial lesion (see Edenbrandt L. et al. in Vectorcardiographic Bites, Journal of Electrocardiology, Vol. 22, Oct. 4, 1989, page 325-331).

Figure 1:
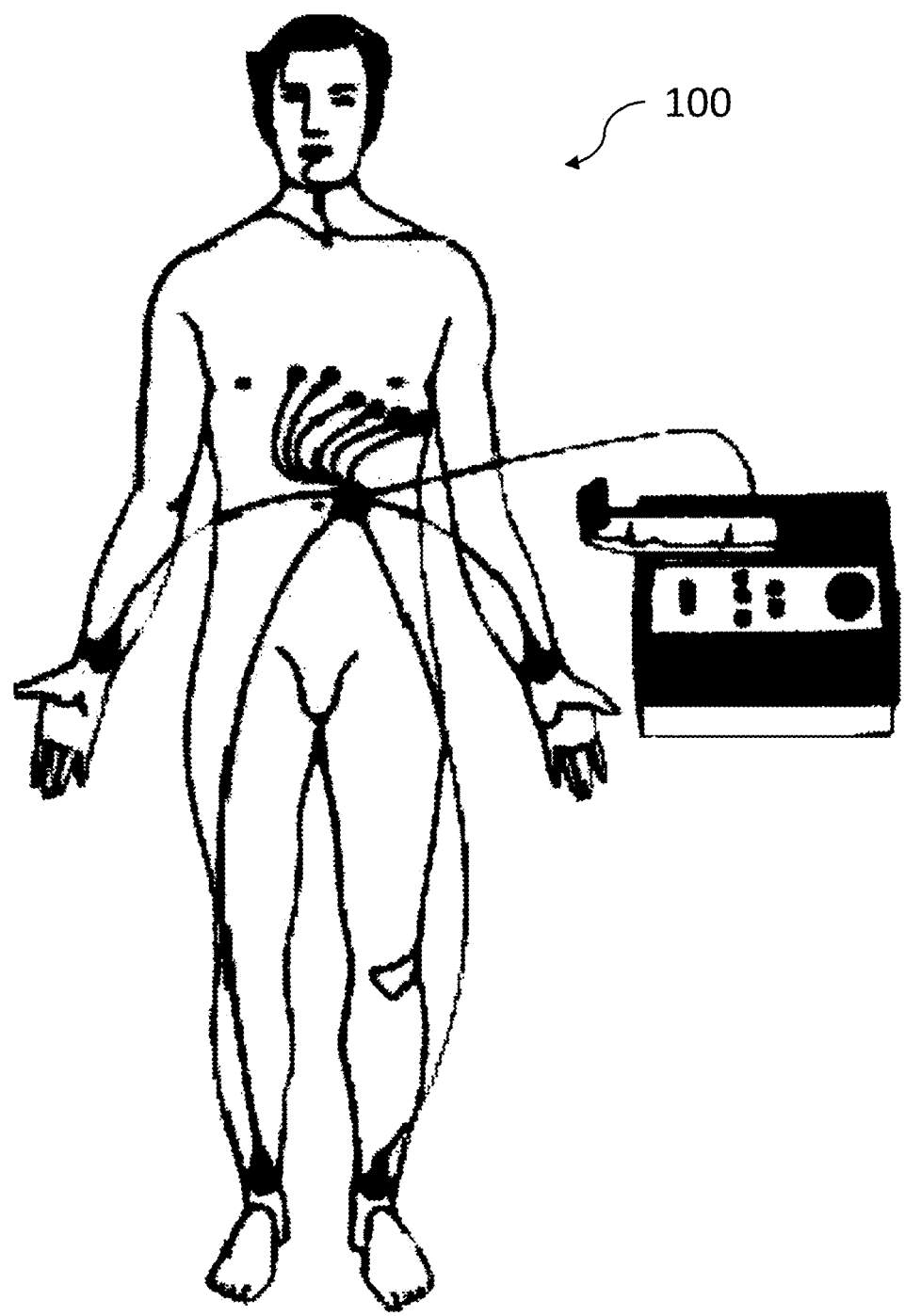
FIG. 1 shows a schematic representation of an electrocardiogram ("EKG") device attached to a human subject to record electrical heart activity.
Figure 2:
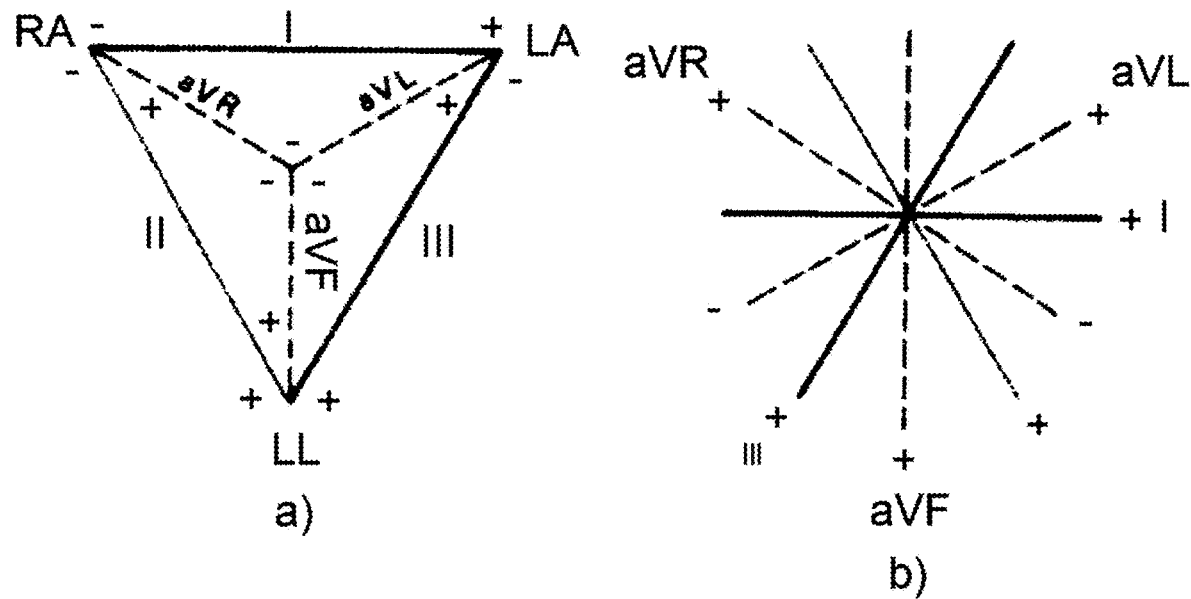
FIG. 2 shows a schematic representation of a triaxial system.
Figure 3:
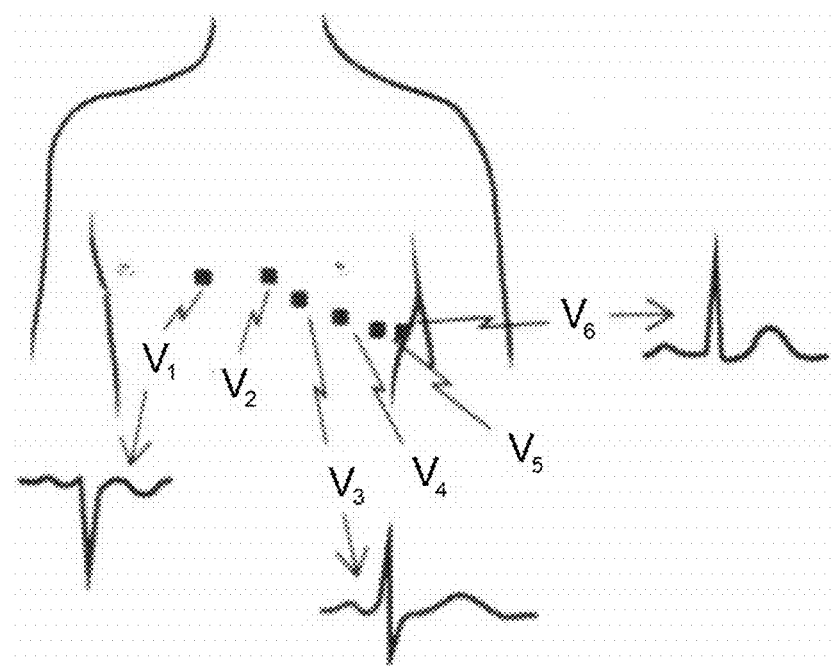
FIG. 3 shows a schematic representation of an order of a precordial electrode system.
Figure 4:
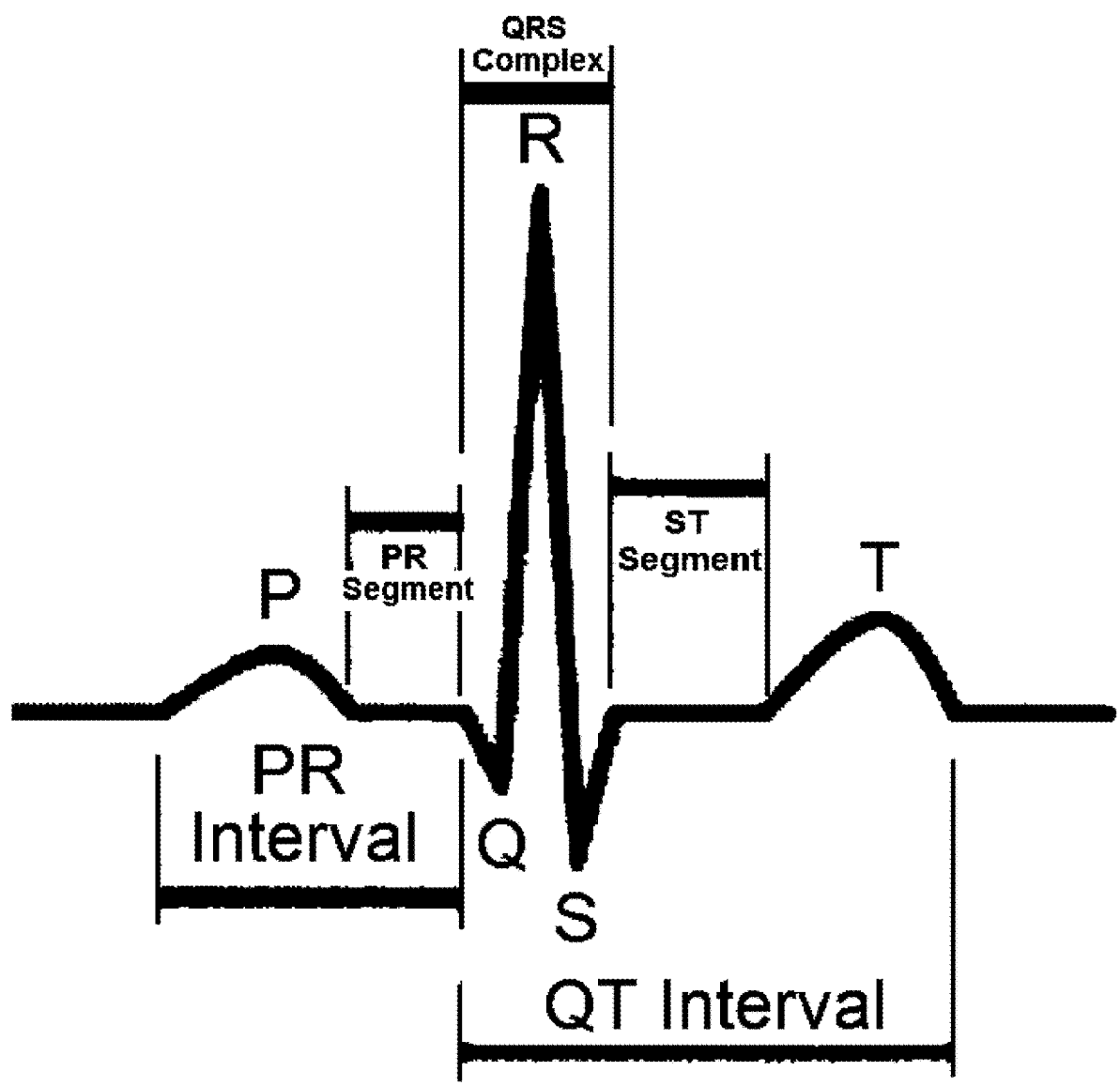
FIG. 4 shows a schematic representation of an appearance of a heart cycle.
Figure 5:
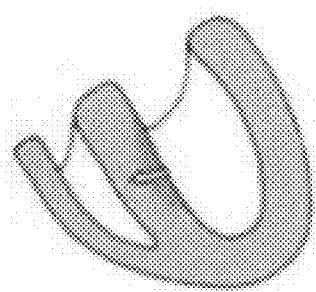
FIG. 5 shows a schematic representation of Einthoven's triangle.
Figure 5:
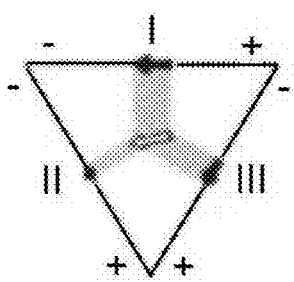
Figure 5:
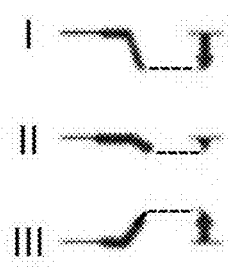
Figure 5:
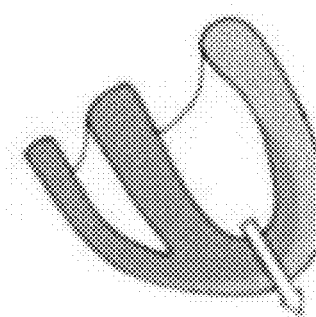
Figure 5:
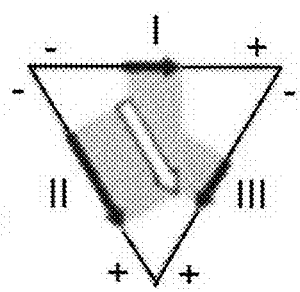
Figure 5:
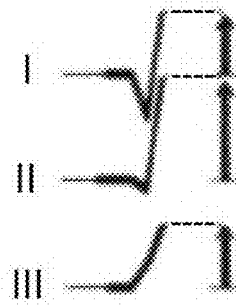
Figure 5:
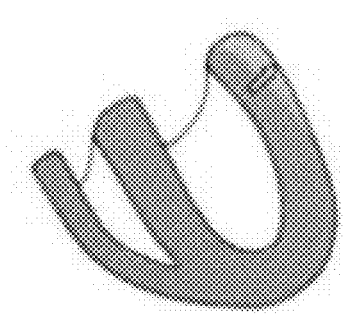
Figure 5:
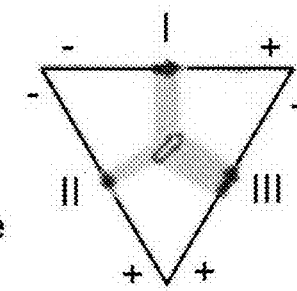
Figure 5:
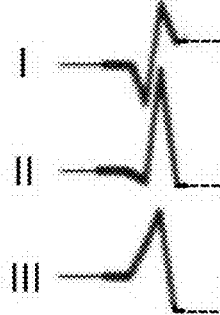
Figure 5:
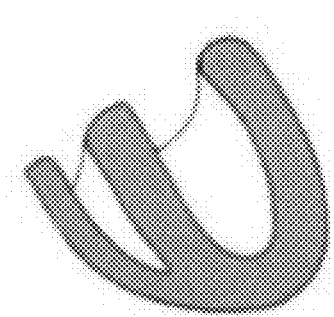
Figure 5:
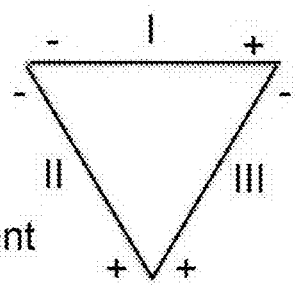
Figure 5:
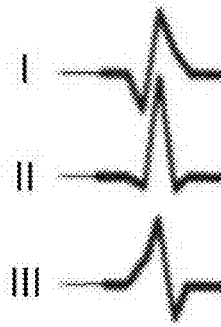
Figure 6:
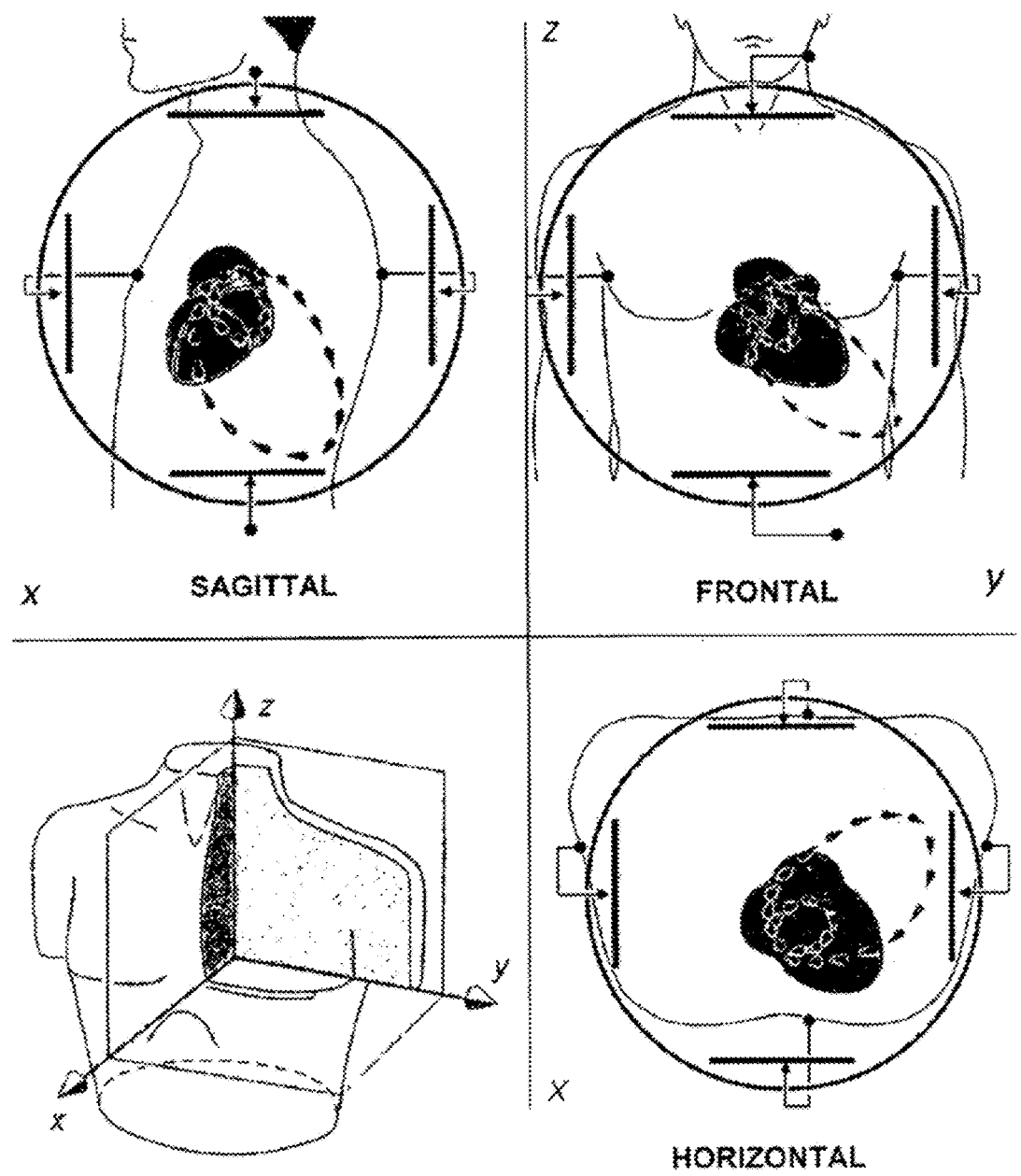
FIG. 6 shows a schematic representation of two-dimensional vector loops in various planes.
Figure 7:
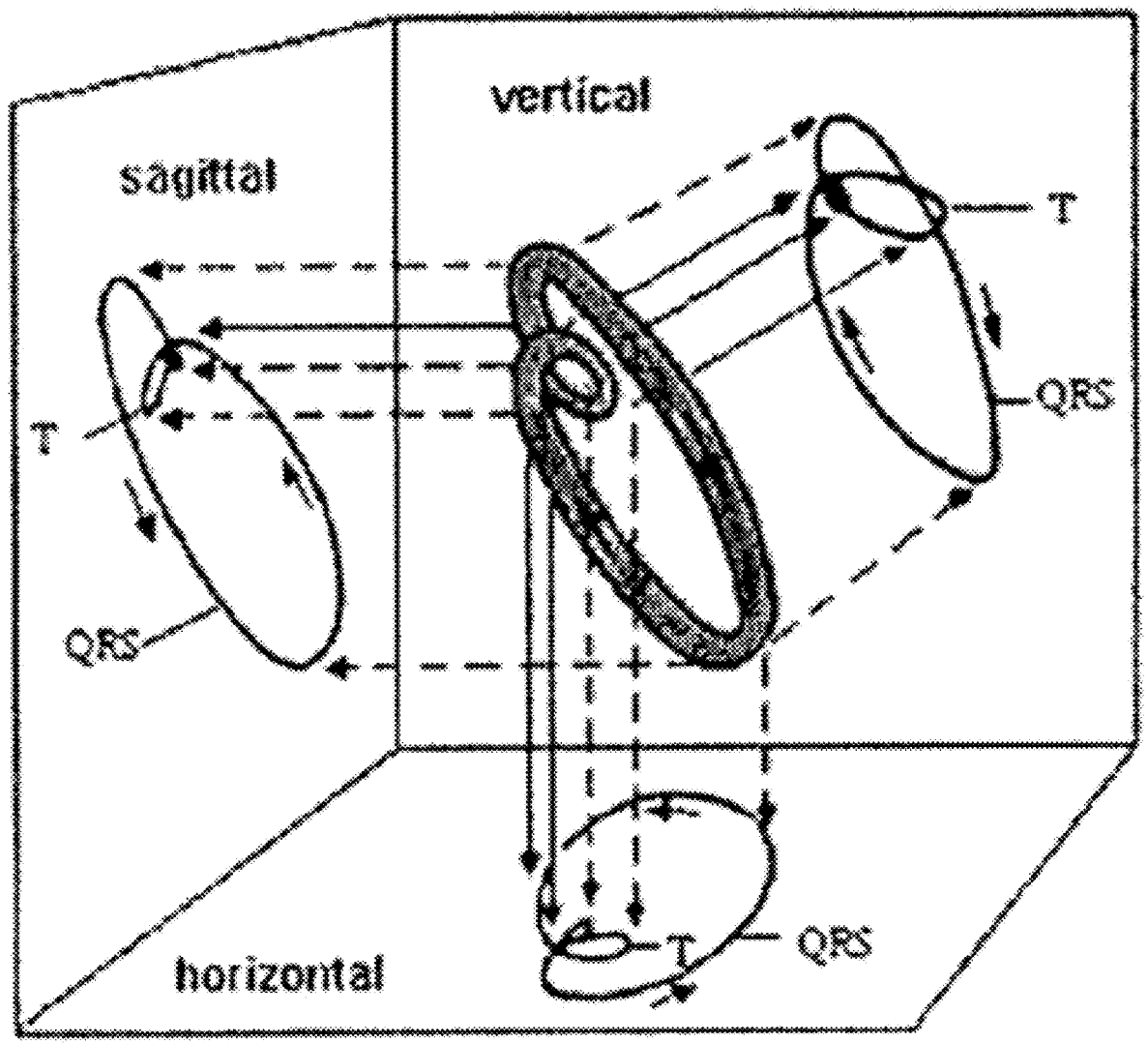
FIG. 7 shows a schematic representation of a three-dimensional vector loop.
Figure 8A:
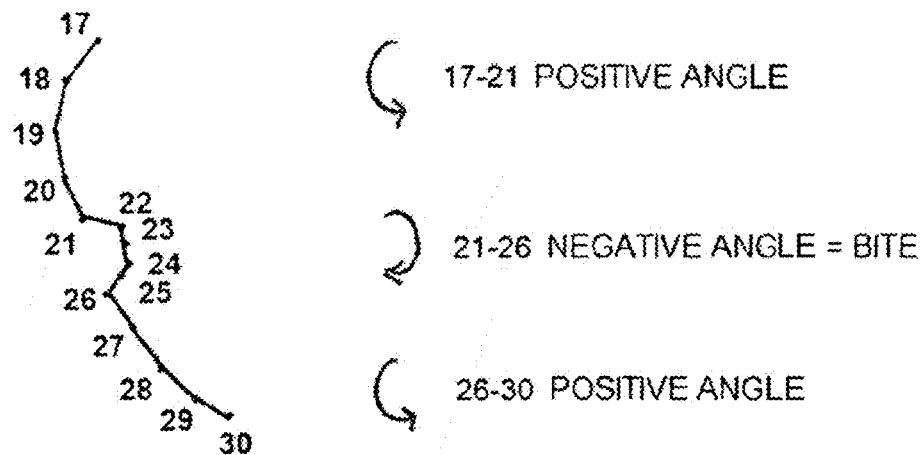
FIG. 8A is a schematic representation of vector loops with a bite.
Figure 8B:
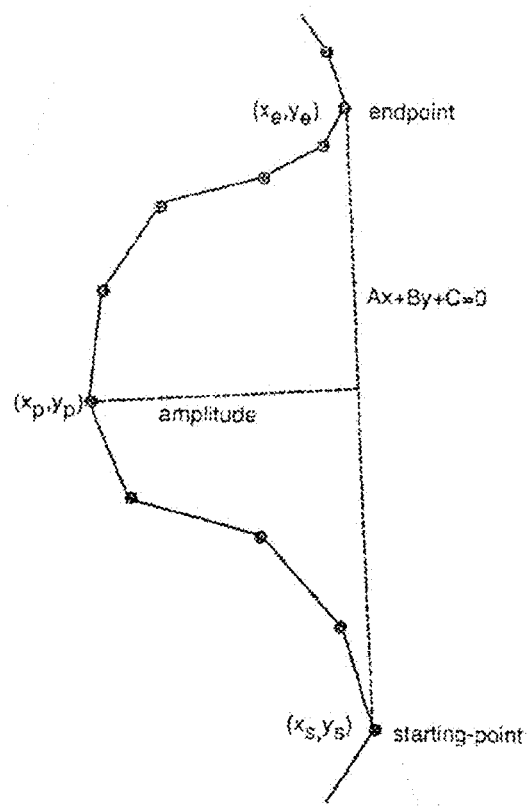
FIG. 8B is a schematic representation of bite amplitude.

A microscar or bite is present when a sector (or portion) of a vector loop changes its direction in contra route in comparison to the rest of major loop (e.g., a sector that rotates clockwise, unlike the rest of loop that rotates counterclockwise). A sector is divided by several points, where three points define an angle that is used to determine whether a sector of a loop rotates counterclockwise or clockwise. An angle retains a positive value if it rotates counterclockwise (e.g., points 17-21 and points 26-30, as shown in FIG. 8A) and takes a negative value if it rotates clockwise (e.g., points 21-26, as shown in FIG. 8A). Through analysis of segments of the vector loop, the existence of a bite between points 21 and 26 can be established (e.g., with probability of 95%). Each bite can be characterized by its amplitude, which is defined as the longest distance between the vector loop and a line extending from a bite start-point to a bite endpoint (as shown in FIG. 8B), with a corresponding duration and area. Normal limits for bite amplitude are 0.12 mV in a horizontal plane and 0.14 mV in a sagittal plane, with a duration of 22 msec (in the horizontal and sagittal planes) and with an area of 15% in the horizontal plane and 23% in the sagittal plane (e.g., as indicated in Edenbrandt L. et al.).

Vector analysis of electrocardiograms for assessment of risk for SCD is accomplished by post-processing of an electrical heart signal after acquisition on an EKG device. In particular, the QRS loop (or portion) is analyzed for characteristic changes in shape that are associated with an early non-manifest phase of ARVD/C in persons prone to hereditary SCD. This method includes automatic analysis, for example, for pattern recognition of a shape of translatory trajectory of aggregate vectors in time and space that occurs in an arrhythmogenic right ventricular dysplasia/cardiomyopathy. This method can be used after signal acquisition from an EKG device, or alternatively during signal acquisition as a part of the EKG device. For example, existing EKG devices can be upgraded to perform this method.

This method can be used for timely recognition of persons with a risk of SCD within otherwise healthy population (e.g., professional athletes and those whose phenotype gene expression is conditioned by environment and life or work circumstances). Gene mutation, which can be responsible for SCD, has no influence on this method. A non-manifest phase of ARVD/C is detectable via this method in an otherwise healthy person.

A method for vector analysis of an EKG for assessment of risk of SCD due to arrhythmogenic right ventricular dysplasia/cardiomyopathy by quantifying micro scars in three-dimensional vector loops includes collecting heart electrical activity information recorded on EKG, generating a vector cardiogram ("VCG") based on the collected information, analyzing the VCG to determine an existence of arrhythmogenic right ventricular dysplasia/cardiomyopathy by quantifying micro scars in a three-dimensional vector loop, and determining whether a risk of SCD is established based on the analysis of the VCG. The results can be stored, optionally with personal and other diagnostic data about patient, in a database for further use.

The collection of heart electrical activity information recorded on EKG can be done either online or offline. Online collection of heart electrical activity information can be done by direct loading from an EKG device or by remote loading. Offline collection of heart electrical activity information can be done either by scanning EKG print out or loading of stored data.

For data collection that is done by scanning, a picture of a scanned EKG tracing is selected, after which a manual or automatic search of the EKG information, specifically leads and lead set up, is performed, where leads lines are matched up to particular leads from drop down menu. Alternatively, electrical heart activity of heart can be acquired by VCG device.

In another method for vector analysis of an electrocardiogram for assessment of risk of SCD due to arrhythmogenic right ventricular dysplasia/cardiomyopathy by quantifying micro scars in one or more three-dimensional vector loops, either online data or offline data loading is selected. If online data loading is selected, then either direct data loading or remote data loading is selected. If direct data loading is selected, then the data is loaded by directly accessing an EKG device. If remote data loading is selected, then the data is loaded by a wireless connection. If offline data loading is selected, data is loaded either by scanning EKG information or loading stored data.

Once the data has been loaded, either a manual search or an automatic search is selected to determine adequate EKG leads. If a manual search for EKG leads is selected, EKG leads are selected in a consecutive fashion. The selected lead is analyzed further to identify potential errors and finding key features, including a horizontal null, a beginning of a Q part of loop, a beginning of an R part of loop, and a beginning and end of an S part of loop. If an automatic search for EKG leads is selected, then three or more leads are selected at the same time by the software.

Stored data from a suitable archived database is loaded, and a VCG is plotted by application of an inverse orthogonal projection that converts a two-dimensional VCG into a three-dimensional VCG (e.g., a three-dimensional loop) and separate pieces of the Q, R and S sections of the loop are identified.

After acquiring a resulting vector loop, some additional transformations and adjustments can be performed for additional analysis. For example, the loop can be magnified, decreased, or rotated.

Data consistency can be checked to determine if there is any deformation (or corruption). If there is deformation, further analysis is abandoned, and an error is registered. If the data is not corrupted, it can be searched for signs of the disease, such as a manifest and obvious phase of the disease. If signs of the disease are found, then a risk of SCD is established. If no signs of disease are found, then the S portion of the loop can be evaluated to determine deviation from an expected trajectory or shape. If deviation is determined to be higher than expected or in a defined range, then a risk of SCD is established. If deviation is determined to be within expectations or within a defined range (e.g., a defined epsilon environment a defined limit), then an R portion of the loop can be analyzed for an indication of potential risk of SCD.

Figure 10:
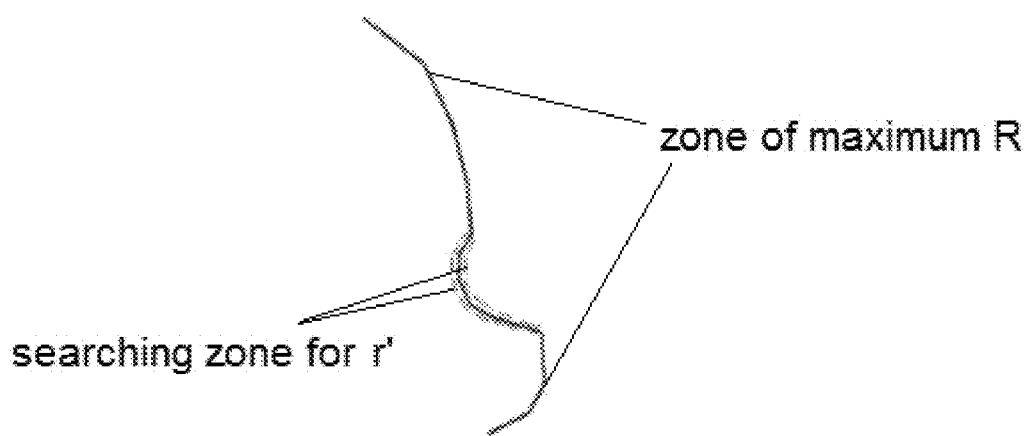
FIG. 10 shows a schematic representation of a deviation of expected itinerary.
Figure 11:
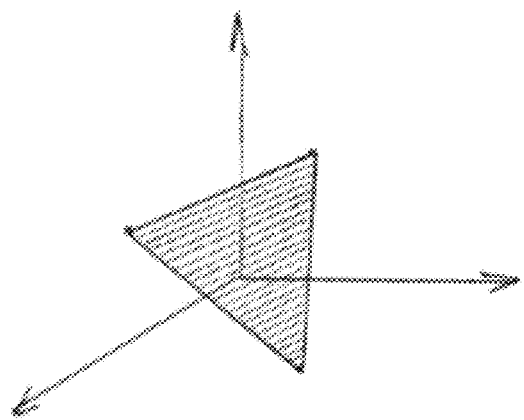
FIG. 11 shows a schematic representation of an axonometric transformation of loop projections on a plane.

The R portion of the loop can be obtained from an axonometric transformation of the R waves from all 12 EKG leads combined together at the same instant. In other words, a two-dimensional ("2D") EKG view usually gives an aspect of just one R peak (wave) present, even if there is rR' or Rr' (second letter is indexed as prime) visible on a three-dimensional ("3D") VCG axonometric transformation. However, a determined axonometric transformation of the R portion (e.g., a zone of maximum R) of a 2D EKG can be performed or selected for an optimal view for a particular micro scar (e.g., searching zone for r'), as shown in FIG. 10. For example, the axonometric transformation can be analyzed for rR' (i.e., micro r/large R format), Rr' (i.e., large R/micro r format), and/or an abrupt change of itinerary (or direction) of a vector of a loop section that has an increasing or decreasing R portion on one of the infinitive number of 2D planes, as shown in FIG. 11. If an adequate quantitative cut off R' peak value is found positive for deflection, as show in FIG. 12, a risk of SCD is established.

For example, as EKG data is a combination of twelve drains which represent a combination of Eintoven's triangle (i.e., potential differences from the place of recording) and represent the view angle of a 3D vector loop, a VCG based on the EKG data from the twelve drains has multiple (e.g., at least three) EKG overviews because of the multiple planes of view (e.g., the three different orthogonal views). Microscars (i.e., "bites") are isolated in some parts of the QRS loops, but not in the last 40-50 msc. For example, the microscars can be observed in the QRS complex, including an upstream R portion (or wave) as well as a downstream S portion (or wave). In a typical amplification of a two-dimensional depiction of a QRS complex (e.g., 100 times multiplication), these fine changes are difficult to observe, but they can be identified with a 3D VCG.

In an example, simultaneously acquired EKG data (i.e., the data from each of the twelve EKG drains) can be transformed into a VCG, where the information from the EKG data is not altered or lost such that a microscar can be observed. For example, a presence of a microscar is maintained when the simultaneously acquired EKG data is transformed. In other words, the presence of the microscar is not obscured. As a result, the microscar is detectable in the 3D view.

A system for vector analysis of electrocardiogram in assessment of risk of SCD due to arrhythmogenic right ventricular dysplasia/cardiomyopathy by quantifying micro scars in three-dimensional vector loops includes a unit for collecting data about electrical activity of the heart recorded on an EKG, a unit for generating a VCG based on collected data, a unit for performing an analysis of the obtained VCG in order to discover arrhythmogenic right ventricular dysplasia/cardiomyopathy by quantifying micro scars in the three-dimensional vector loop, and a unit for storing a result of the analysis of the obtained vector cardiogram, optionally together with personal and other diagnostic data about patient, in a database for further use. The units can be a personal computer, and the system can be integrated in an EKG device.

Figure 9A:
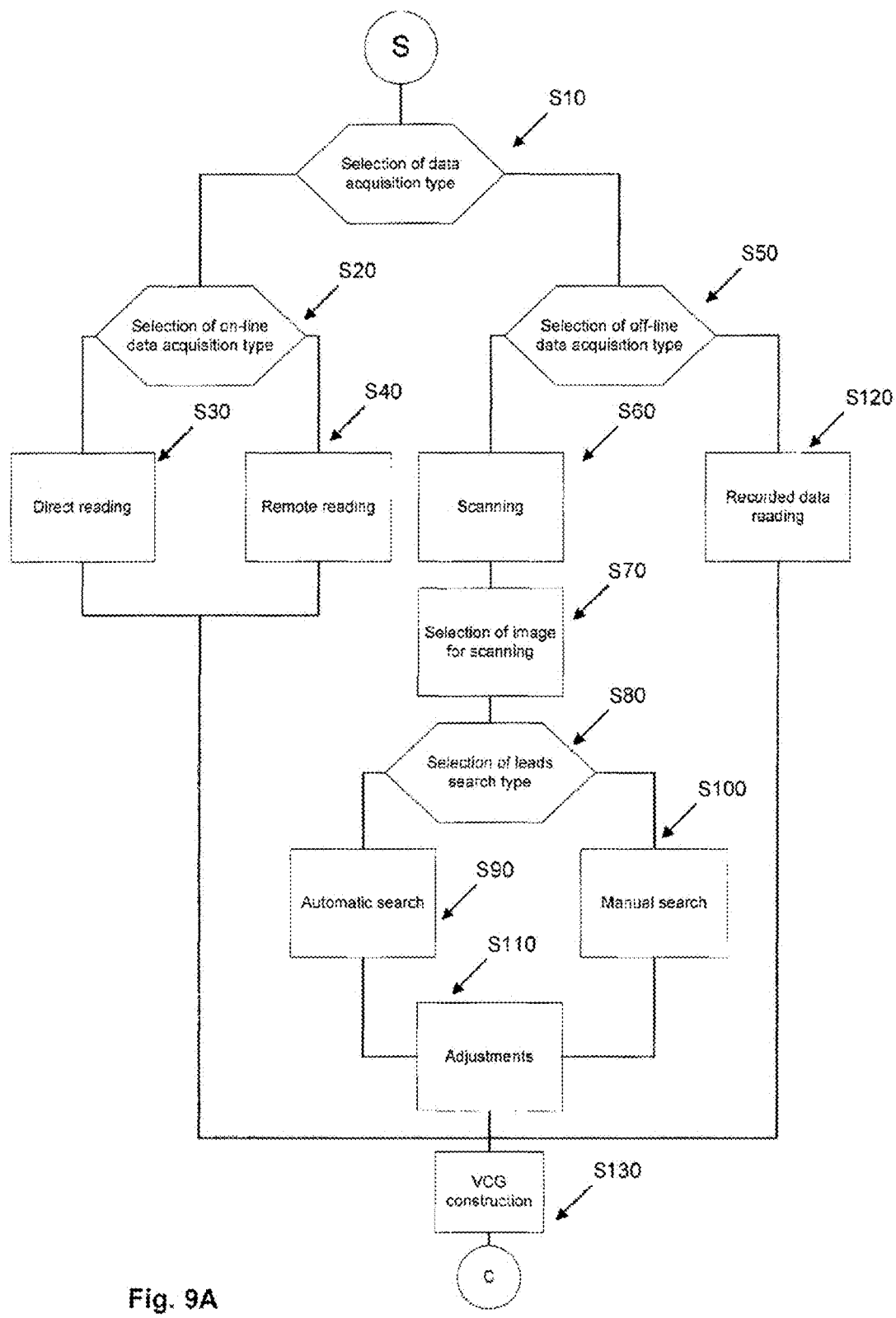
FIG. 9A shows a flow chart of vector analysis of an EKG.
Figure 9B:
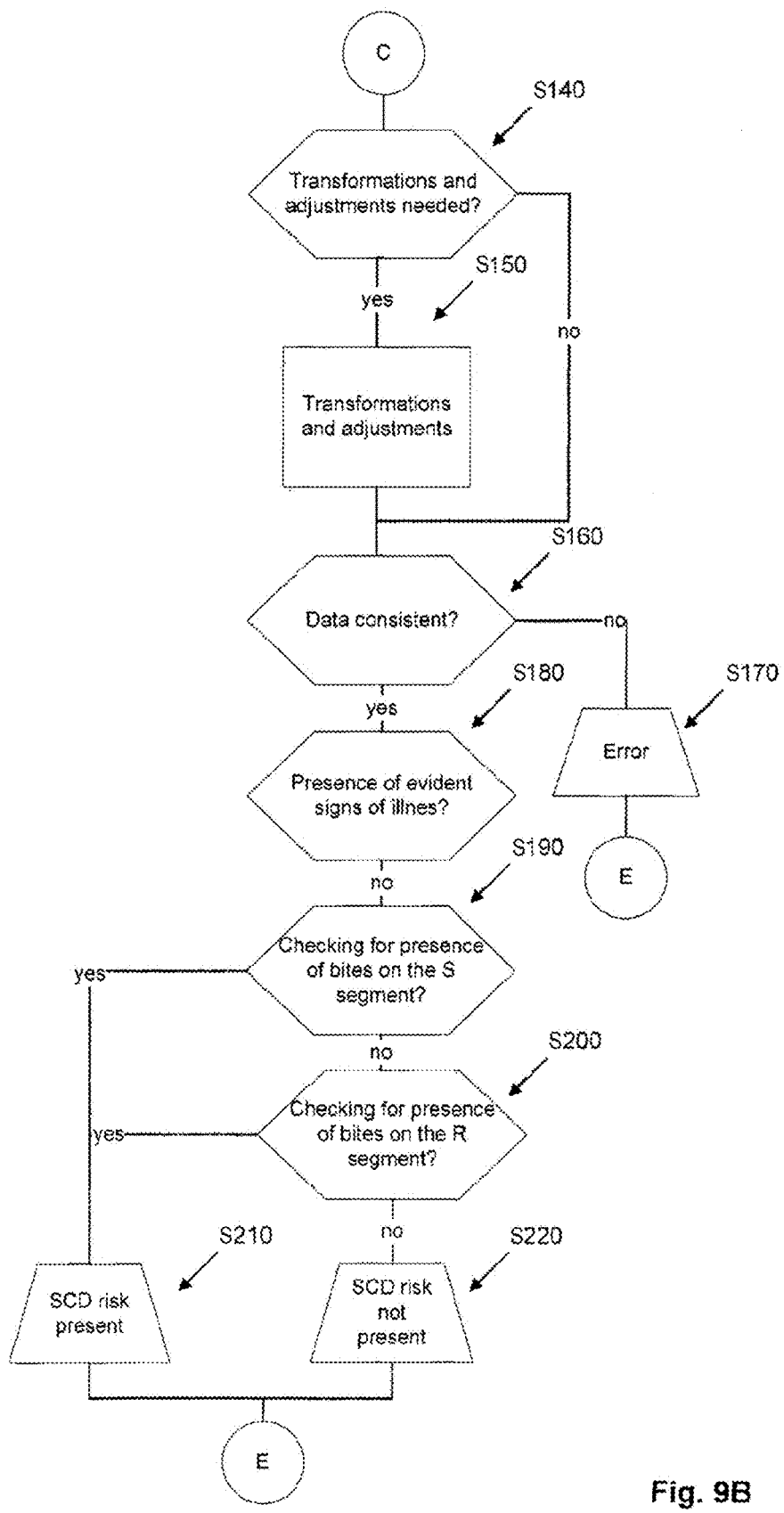
FIG. 9B shows a flow chart of vector analysis of an EKG.

As shown in FIGS. 9A and 9B, a method for vector analysis of an electrocardiogram in assessment of a risk of sudden cardiac death (SCD) due to arrhythmogenic right ventricular dysplasia/cardiomyopathy by quantifying micro scars (i.e. "bites") in three-dimensional vector loops according to the invention which achieves the recognition of arrhythmogenic right ventricular dysplasia/cardiomyopathy (and similar congenital states) that cause sudden cardiac death in an otherwise healthy population is disclosed herein. The steps of the method include selecting a way of data downloading (or selection of a data acquisition type) at step S10. In step S10, the choice of a way of data downloading that is necessary for this procedure is particularized. The signal acquisition is a process of accessing the information needed for further diagnostics. EKG information could be accessed from several sources. Thus, for example, new findings can be acquired directly from an apparatus, or from the picture of existing findings. Digitally stored findings may also be used. Data downloading could be in real time, i.e. online, or previously obtained data may be used, i.e. offline acquiring can be performed. Later steps can depend on the selected way of loading.

If on-line data downloading S20 is selected, then either direct data downloading S30 or remote data downloading S40 is selected. Later steps can depend on the selected way of loading.

If direct data downloading (direct reading) S30 is selected, then it is possible by using different streams, necessary because of the diversity of EKG devices, to access data directly from EKG apparatus. Streams (wire connections) are made by manufacturer companies or in agreement with them. In the case of direct data downloading, an EKG device is in direct contact with a personal computer, which contains the appropriate software for executing the analysis method described herein. Physical connection can be achieved by cables, by using more than one standard way such as serial port, parallel port, USB and similar.

If remote data downloading (remote reading) S40 is selected, then it is generated through some way of wireless connection. As such, there are different standards for wireless connection with PC, such as WiFi, Bluetooth, infrared and similar.

If off-line data downloading (selection of off-line data acquisition) S50 is selected, the selection between scanning of EKG findings S60 or downloading stored data (recorded data reading) S120 is then selected.

If scanning S60 is selected, then it is performed by scanner which can be an optical input device that allows raw data, such as drawings, photo or text to be transferred in suitable form of digital information. It may be necessary to scan EKG findings in a perpendicular manner A suitable picture is selected for scanning S70 that allows EKG findings to be loaded, such as digitally generated findings or a quality scanned picture of the existing EKG findings on paper. EKG findings can be digitalized in any form of the usual picture formats. For acquisition, more than one picture can be used at once if scanning is done in several parts or for comparative purposes.

After picture selection and scanning, it is necessary to find suitable EKG leads S80, either by automatic search S90 or manual search S100.

If a manual search S100 is chosen, a first picture color and lightness of the scanned EKG can be modified. Channels are selected by user. Leads are found consecutively.

If an automatic search S90 is chosen, an automatic search for the leads is executed. Considering that leads on EKG findings are organized by groups of three leads, it enables three or more leads to be found at the same time.

After the leads are obtained (either by manual or automatic search), the acquired leads can be adjusted S110 for elimination (or reduction) of errors and finding key points Q,R,S by approximating data from all leads simultaneously. Horizontal null is automatically adjusted, but can be also manually fitted. Other key points are related to QRS complex, including a starting point of Q part of loop, a beginning of R part of loop, and a beginning and end of S part of loop. Those can be automatically found or set manually.

If a way of downloading stored data S120 is selected, the stored data can be downloaded from a suitably archived database. The type of archived database depends on the type of acquisition. If acquisition was made from a device, then it is necessary to record the finding first. If acquisition was made from a picture, it was adjusted as explained in steps S60-S100.

After the data is acquired, a VCG is plotted S130, for example, by transformation from EKG to VCG by application of an inverse orthogonal projection that converts a two-dimensional VCG into a three-dimensional VCG. After the vectors which define the three-dimensional loop are generated, the loop is plotted, representing Q, R and S parts of loop (e.g., as colored parts).

The three-dimensional VCG can then be checked to determine whether transformations and adjustments are needed at step S140. The desired transformations and adjustments S150 can then be made. For example, after generating vectors for plotting the loop, it is possible to transform the loop in several ways, such as magnifying or decreasing the loop. It is also possible to move the loop in the plane of view for easier magnifying of desired parts. Also, it is possible to rotate the loop for a full circle in all three-dimensions. It is possible to choose what is plotted, i.e. which parts of Q, R and S and the rest of loop are plotted. The transformations and adjustments do not influence the diagnostics, but serve only for a better view of loop.

The data is checked for consistency in EKG-derived information in different leads at step S160. If there is inconsistent data, then it is rejected and an error is reported step S170 is reported so further analysis can be performed. Checking of general superposition between QRS complexes is made in a similar manner.

If step S160 confirms that the data is consistent, a search for the signs of the disease (or illness) is performed at step S180, such as a manifest and obvious phase of the disease. For example, isolated dilatation of the right chamber, where wall thinning and fibro-fatty infiltration of the free heart wall with partial loss of contractility and ballooning effect ("bulging" in systole (that is in the heart cycle phase in which the heart contracts)) is present, can be detected by A) heart ultrasound (echocardiography examination), B) nuclear magnetic reso-nance of the heart or C) by heart biopsy, e.g., of the right side the heart. If these signs are found, diagnostics end and the result is positive, i.e., risk for SCD is recognized at step S210.

If the step S160 did not indicate signs of disease, then the S part of the loop is checked for deviation from an expected trajectory (i.e., checked for the presence of bites) at step S190. An example deviation from an expected trajectory is shown in FIG. 10. The presence of a deviation is determined by comparing a length of the S part of the loop with a defined limit set in a database. If a deviation is outside of the defined limit, the diagnostics terminate and the result is positive, i.e. risk of SCD is established at step S210. If deviations from an expected trajectory are within the defined limit, the R part of the loop is checked for bites S200. If the presence of bites on the R part are detected, then a risk of SCD is established at step S210. If the presence of bites on the R part is not detected, then a risk of SCD is not established S220. The additional evaluation S200 is executed to reject false positive cases (e.g., because a deviation is slightly smaller than a defined limit) or false negative cases (e.g., because a deviation is slightly bigger than a defined limit).

Figure 12:
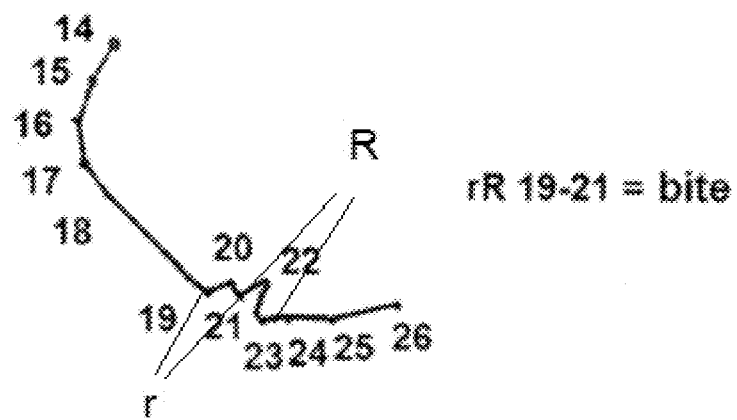
FIG. 12 shows a schematic representation of peaks r'R or Rr in a heart cycle.

If deviations are within the defined limit for the S part of the loop in step S190, the R part of the loop is checked for deviations from an expected trajectory (checked for the presence of bites) in step S200. The R part of loop is checked from an axonometric transformation of the loop (see FIG. 11—illustration in relation to the 3D), where the axonometric transformation provides an optimal 2D view of a bite and is utilized to search for peaks rR' or Rr' and/or an abrupt change of itinerary (or direction) of a vector sector loop for an increasing or decreasing R part. For example, as shown in FIG. 12, a first declination (or deviation) r occurs from 19-21, and a next declination (or deviation) R occurs from from 21-23. A surface area of r is crucial for adequate size of the bite that adds, and it is denoted as bite rR from 19-21. If an r peak is found (as shown by the dotted line in FIG. 10 as the searching zone for r'), the result is positive and risk of SCD is established S210. If answer is negative or if nothing was found, the diagnostic procedure terminates, the result is negative and no risk of SCD is established S220.

Obtained results together with personal and other diagnostic data about the patient can be stored in a database for further use.

The procedure according to the invention represents the basis of making suitable software which would provide the estimation of grounds for sudden cardiac death SCD due to arrhythmogenic right ventricular dysplasia/cardiomyopathy by quantifying micro scars (i.e. "bites") in three dimensional vector loops in reliable and repeatable way. Accordingly, the subject invention in the first place has its use in the field of medicine, especially in medical diagnostics.

It is understandable that on the basis of the description of this invention different kinds of performing the procedure and system according to the invention can be realized, while remaining within the scope of the invention which is defined in the attached patent claims.

It is claimed:

1. A method stored on a non-transitory medium and performed by a processor for three-dimensional vector analysis of an electrocardiogram in search for micro-scar ("bite") in a three-dimensional vector loop for assessment of sudden cardiac death (SCD) risk in arrhythmogenic right ventricular dysplasia/cardiomyopathy based on presence of micro-scar ("bite"), the method comprising:

receiving electrocardiogram (EKG) waveform data from twelve leads of EKG recording of a patient's heart activity as one of a real time recording, or from an EKG print out, and an EKG image;

generating a three-dimensional vectorcardiogram (VCG) based on the received EKG waveform data by transformation of the twelve EKG leads by application of inverse orthogonal projection that converts a two-dimensional VCG into a three-dimensional VCG;

analyzing the three-dimensional VCG to identify the presence of a micro-scar ("bite") in the three-dimensional vector loop without time delay which is achieved by setting borders for a beginning of a Q part, an R part, and an S part, and an end of the S part, of the three-dimensional vector loop from the twelve EKG leads;

determining the SCD risk in arrhythmogenic right ventricular dysplasia/cardiomyopathy for the patient based on the identification of the presence of micro-scar ("bite") in the three-dimensional vector loop; and storing, in a database, the SCD risk in arrhythmogenic right ventricular dysplasia/cardiomyopathy based on the presence of micro-scar ("bite") in the three-dimensional vector loop.

2. The method according to claim 1, wherein analyzing the three-dimensional VCG comprises:

searching for a plurality of micro-scars ("bites") where each micro-scar from the plurality of micro-scars ("bites") represents deviation from an ideal curve as observed in the three-dimensional vector loop in a pre-defined region of one of the S part and the R part, of the three-dimensional vector loop;

when analyzing the S part of the three-dimensional vector loop to determine a deviation from expected trajectory, if a trajectory of the S part is out of range of preset limit of epsilon environment a deviation representing the presence of micro-scar ("bite") is determined and the SCD risk in arrhythmogenic right ventricular dysplasia/ cardiomyopathy is established and the search terminates, if not, the search continues for the R part of the three-dimensional vector loop for detection of the presence of micro-scar ("bite");

when deviation of the trajectory of the S part is determined to be within a defined epsilon environment, which is a preset limit stored in software code, analyzing process for the R part of the three-dimensional vector loop continues in search for the presence of micro-scar ("bite") indicative of the SCD risk in arrhythmogenic right ventricular dysplasia/cardiomyopathy, which is done by searching for an rR' of the R part as an abrupt change of direction in one of a negative rotation and a clockwise rotation of the three-dimensional vector loop; and when the abrupt change of direction of the rR' of the R part of the three-dimensional vector loop is found, the SCD risk in arrhythmogenic right ventricular dysplasia/ cardiomyopathy is established and the search for the plurality of micro-scars ("bites") terminates.

3. The method according to claim 1, wherein the EKG waveform data is received off-line as from previously obtained EKG waveform data from the EKG recording of the patient's heart activity as at least one of the EKG print out and the EKG image.

4. The method according to claim 1, wherein the EKG waveform data is received via loading of stored EKG data from a database as at least one of a scan of the EKG print out and the EKG image, wherein the EKG waveform data is loaded to software code.

5. The method according to claim 1, wherein the EKG waveform data is received via downloading of recorded EKG waveform data as the EKG image from an external database.

6. The method according to claim 4, wherein the loading of the stored EKG data comprises at least one of software code and manual corrective option for:
   selecting of individual EKG waveform data for analysis and setting the borders of the beginning of the Q part, the R part, and the S part, and the end of the S part, of the three-dimensional vector loop, based on the analysis of the selected individual EKG waveform data; and
   identifying the borders of the beginning of the Q part, the R part, and the S part, and the end of the S part, of the three-dimensional vector loop, based on the analysis of the selected individual EKG waveform data.

7. The method according to claim 1, wherein the EKG waveform data is received online, wherein data of the patient's heart activity is received in real time from an electrocardiogram device when transmitted one of wirelessly and through a wire connection.

8. The method according to claim 7, wherein the EKG waveform data is received from the electrocardiogram device, wherein the electrocardiogram device is serving as a platform incorporated software for detection of the SCD risk in arrhythmogenic right ventricular dysplasia/cardiomyopathy based on one of the presence of micro-scar ("bite") in three-dimensional vector loop and a monitor connected to the patient with the incorporated software.

9. A method stored on a non-transitory medium and performed by a processor for three-dimensional vector analysis of a two-dimensional vectorcardiogram in search for micro-scar ("bite") in a three-dimensional vector loop for assessment of sudden cardiac death (SCD) risk in arrhythmogenic right ventricular dysplasia/cardiomyopathy based on presence of micro-scar ("bite"), the method comprising:
   obtaining electrical activity data of a patient's heart activity recorded on a vectorcardiography device as a two-dimensional vectorcardiogram;
   generating the three-dimensional vector loop based on the two-dimensional vectorcardiogram via an inverse orthogonal projection, wherein a Q part, an R part and an S part, of the three-dimensional vector loop are delineated;
   analyzing the three-dimensional vector loop to identify the presence of micro-scar ("bite") in the three-dimensional vector loop in a predefined region of one of the S part and the R part, of the three-dimensional vector loop;
   determining the SCD risk in arrhythmogenic right ventricular dysplasia/cardiomyopathy for the patient based on the identification of the presence of micro-scar ("bite") in the three-dimensional vector loop; and
   storing, in a database, the SCD risk in arrhythmogenic right ventricular dysplasia/cardiomyopathy based on the presence of micro-scar ("bite") in the three-dimensional vector loop.

\* \* \* \* \*